United States Patent [19]

Preston

[11] Patent Number: 5,616,814
[45] Date of Patent: *Apr. 1, 1997

[54] METHOD FOR THE WATER WASHING AND RECOVERY OF METHYL TERTIARY BUTYL ETHER

[75] Inventor: Kyle L. Preston, Port Arthur, Tex.

[73] Assignee: Texaco Chemical Inc., White Plains, N.Y.

[*] Notice: The term of this patent shall not extend beyond the expiration date of Pat. No. 5,457,243.

[21] Appl. No.: 516,373

[22] Filed: Aug. 17, 1995

[51] Int. Cl.⁶ .............................. C07C 41/05; C07C 41/09
[52] U.S. Cl. .............................. 568/699; 568/697; 568/698
[58] Field of Search .............................................. 568/699

[56] References Cited

U.S. PATENT DOCUMENTS 5,457,243  10/1995  Knifton et al. ........................ 568/697

Primary Examiner—José G. Dees
Assistant Examiner—Dwayne C. Jones
Attorney, Agent, or Firm—Henry H. Gibson; Harold J. Delhommer; James L. Bailey

[57] ABSTRACT

An improved method of recovering methyl tertiary butyl ether from an etherification reaction product containing acidic by-products wherein the reaction product is charged to an MTBE distillation zone and fractionated therein to provide a lower boiling distillation fraction comprising isobutylene, methyl tertiary butyl ether, methanol and acidic by-products, wherein the lower boiling distillation fraction is counter-currently washed with alkaline water in a methanol extraction tower, and wherein an aqueous solution of an alkali is injected into the tower below the charge point for the wash water to substantially completely neutralize the acidic by-products and to provide an overhead extract substantially free from acidic by-products comprising isobutylene, methyl tertiary butyl ether and a minor amount of water, and a bottoms raffinate comprising methanol, water, alkaline by-products and a minor amount of methyl tertiary butyl ether.

9 Claims, 1 Drawing Sheet

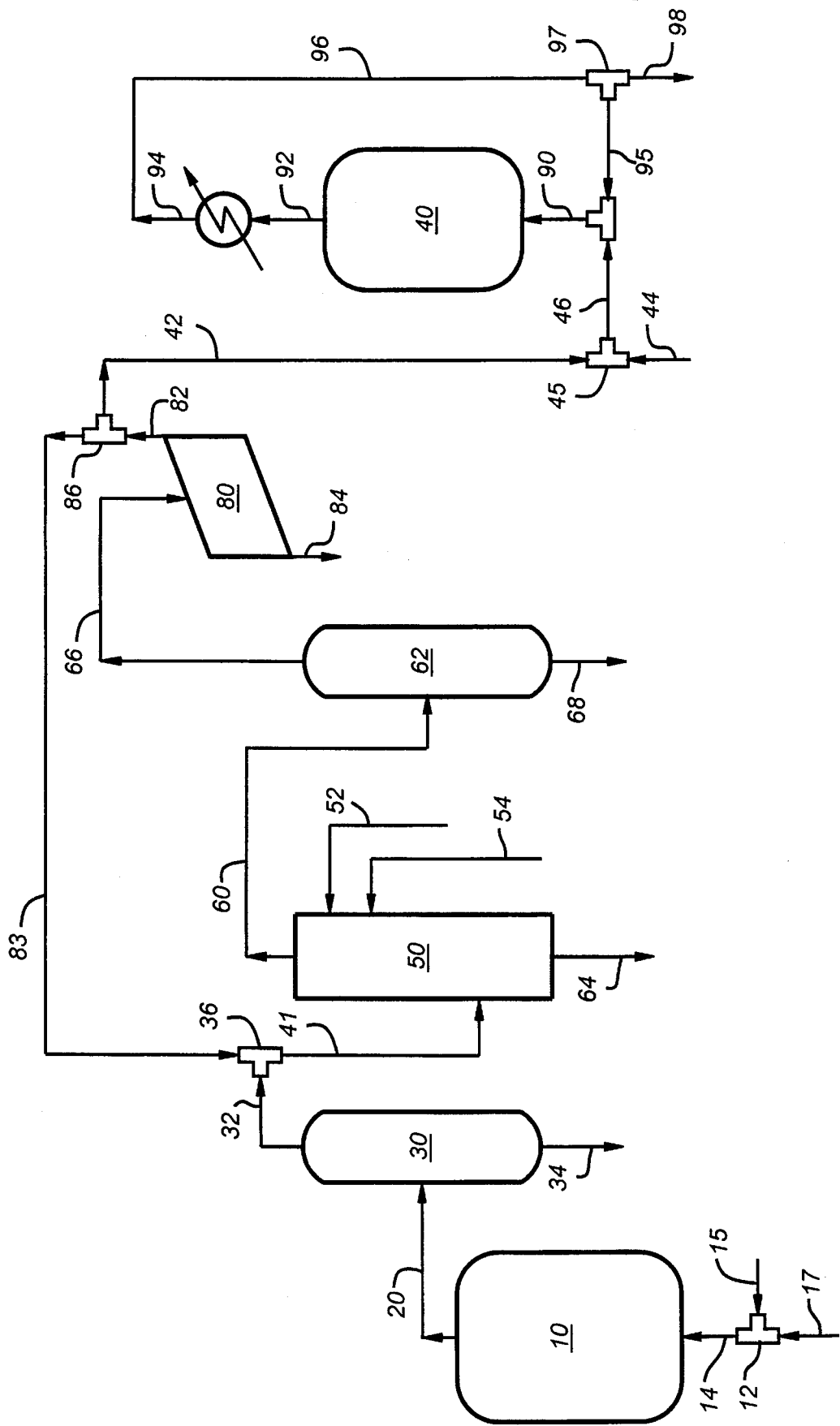

METHOD FOR THE WATER WASHING AND RECOVERY OF METHYL TERTIARY BUTYL ETHER

BACKGROUND OF THE INVENTION

1. Technical Field of the Invention

This invention relates to a method for the manufacture and purification of methyl tertiary butyl ether. More particularly, this invention relates to a water washing method useful in the purification of the methyl tertiary butyl ether.

Methyl tert-butyl ether is finding increasing use as a blending component in high octane gasoline as the current gasoline additives based on lead and manganese are phased out.

2. Prior Art

In U.S. Pat. No. 4,144,138 (1979) to Rao et al., there is disclosed a method for recovering methyl tertiary butyl ether from an etherification reaction effluent by azeotropic distillation to recover a methanol-ether azeotrope overhead which is water-washed to give pure ether raffinate, the latter being azeotropically distilled to yield ether-methanol overhead which is recycled to water washing.

Kruse et al. U.S. Pat. No. 5,243,091, entitled "Method for the Manufacture and Recovery of Methyl Tertiary Butyl Ether", discloses a method for the preparation of methyl tertiary butyl ether wherein tertiary butyl alcohol is reacted with methanol to provide a reaction product comprising methyl tertiary butyl ether and by-product isobutylene and wherein the by-product isobutylene is reacted with methanol to provide additional methyl tertiary butyl ether and also a water washing method for the purification of the methyl tertiary butyl ether.

Gupta U.S. Pat. No. 5,292,964 discloses a process for the manufacture of methyl tertiary butyl ether from tertiary butyl alcohol and methanol wherein tertiary butyl alcohol is reacted with methanol in a primary reaction zone to provide a reaction product comprising methyl tertiary butyl ether, unreacted tertiary butyl alcohol, unreacted methanol and water, wherein the reaction product is separated in a distillation zone into a lighter fraction comprising substantially anhydrous methanol and methyl tertiary butyl alcohol and a heavier fraction comprising tertiary butyl alcohol, methanol and water, and wherein the lighter fraction is charged to a finishing reactor wherein the methanol is reacted with isobutylene to form additional methyl tertiary butyl ether.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl., Vses. Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process.

In copending Cassata et al. U.S. patent application Ser. No. 08/147,508, filed Nov. 8, 1993, now U.S. Pat. No. 5,395,982 and entitled "Continuous Isobutylene-Assisted Aqueous Extraction of Methanol from Methyl Tertiary Butyl Ether" a process is disclosed wherein an impure methyl tertiary butyl ether product contaminated with isobutylene, methanol and water is purified by continuous counter-current contact with water and with added isobutylene in a counter-current contact extraction tower to provide an overhead extract comprising isobutylene, methyl tertiary butyl ether and water and a raffinate comprising methanol, water and a minor amount of methyl tertiary butyl ether, the overhead extract being separated in a methyl tertiary butyl ether purification distillation zone into a lighter distillation fraction comprising isobutylene and water and a heavier distillation fraction consisting essentially of methyl tertiary butyl ether, the lighter distillation fraction being decanted to remove water and to provide a distillate isobutylene fraction that is returned to the contact tower.

In copending Peters et al. U.S. patent application Ser. No. 08/147,507, filed Nov. 5, 1993, abandoned on Jan. 17, 1995, and entitled "Isobutylene-Assisted Aqueous Extraction of Methanol from Methyl Tertiary Butyl Ether" there is disclosed a process for the manufacture of methyl tertiary butyl ether from tertiary butyl alcohol and methanol and to the purification of a methanol-contaminated methyl tertiary butyl ether intermediate product formed during the process; the intermediate product being purified by counter-current contact with water in an extraction tower, wherein isobutylene is added to the extraction tower to assist in the formation of an extract composed of methyl tertiary butyl ether, isobutylene and water and in the formation of a raffinate comprising methanol, isobutylene, residual methyl tertiary butyl alcohol and water.

SUMMARY OF THE INVENTION

This invention is directed to an improved method of recovering methyl tertiary butyl ether from an etherification reaction product containing acidic by-products including methyl formate, isobutyl formate, t-butyl acetate, etc. It is difficult to remove methyl formate from methyl tertiary butyl ether. In accordance with the present invention, the reaction product is charged to a first MTBE distillation zone and fractionated therein to provide a first lower boiling distillation fraction comprising substantially all of the isobutylene and substantially all of the methyl tertiary butyl ether and some of the methanol and the organic acids and esters in the etherification reaction product and to also provide a higher boiling distillation fraction comprising methanol, tertiary butyl alcohol and water.

The first lower boiling distillation fraction is counter-currently washed with water in a methanol extraction tower and an aqueous solution of an alkali is injected into the tower adjacent the top thereof but below the charge point for the wash water in an amount sufficient to substantially completely neutralize the methyl formate and to thereby counter-currently contact the etherification reaction product to provide an overhead extract comprising isobutylene, methyl tertiary butyl ether and a minor amount of water, and a bottoms raffinate comprising methanol, water, alkali (e.g., sodium formate) and a minor amount of methyl tertiary butyl ether.

In accordance with a preferred embodiment of the present invention, an etherification reaction product is obtained comprising methanol, tertiary butyl alcohol, water, isobutylene, acidic by-products such as organic acids and esters including methyl formate and methyl tertiary butyl ether. The etherification reaction product is charged to a first MTBE distillation zone and fractionated therein to provide a first lower boiling distillation fraction comprising substantially all of the isobutylene and substantially all of the methyl tertiary butyl ether and some of the methanol and the organic acids and esters in the etherification reaction product and to also provide a higher boiling distillation fraction comprising methanol, tertiary butyl alcohol and water.

The first lower boiling distillation fraction is continuously charged to a methanol extraction tower adjacent the bottom thereof;

alkaline wash water is continuously charged to the methanol extraction tower adjacent the top thereof;

an aqueous solution of an alkali is charged to the methanol extraction tower adjacent the top thereof but below the charge point for the wash water, in an Mount sufficient to substantially completely neutralize the methyl formate, to thereby counter-currently contact the first lower boiling distillation fraction to provide an overhead extract comprising isobutylene, methyl tertiary butyl ether and a minor amount of water, and a bottoms raffinate comprising methanol, water, alkali such as sodium formate and a minor Mount of methyl tertiary butyl ether; and the extract is continuously charged to a methyl tertiary butyl ether distillation zone and separated therein into a lower boiling (lighter) distillation fraction comprising isobutylene and water and a higher boiling (heavier) distillation fraction consisting essentially of methyl tertiary butyl ether.

In accordance with another preferred embodiment of the present invention, isobutylene is recovered from the extract and recycled to the methanol extraction tower in order to reduce the amount of methyl tertiary butyl ether exiting the tower with the raffinate.

DESCRIPTION OF PREFERRED EMBODIMENTS

A preferred method for the continuous preparation of methyl tertiary butyl ether from tertiary butyl alcohol, isobutylene and methanol in accordance with the present invention comprises:

a) continuously reacting methanol with tertiary butyl alcohol to form an etherification reaction product comprising methanol, tertiary butyl alcohol, water, isobutylene, acidic by-products, including methyl formate and methyl tertiary butyl ether;

b) continuously charging the etherification reaction product to a first MTBE distillation zone and fractionating it therein to provide a first lower boiling distillation fraction comprising substantially all of the isobutylene and substantially all of the methyl tertiary butyl ether and some of the methanol and the organic acids and esters in the etherification reaction product and to also provide a higher boiling distillation fraction comprising methanol, tertiary butyl alcohol and water;

c) charging the first lower boiling distillation fraction to a methanol extraction tower adjacent the bottom thereof;

d) continuously charging wash water to said methanol extraction tower adjacent the top thereof in the ratio of about 2 to about 10 volumes of the first lower boiling distillation fraction per volume of water under extraction conditions including a temperature of about 20° to about 60° C. and a pressure of about 50 to 500 psia;

e) continuously charging an aqueous solution of an alkali to said methanol extraction tower adjacent the top thereof but below the charge point for the wash water to thereby counter-currently contact the first lower boiling distillation fraction with an amount of aqueous alkali sufficient to substantially completely neutralize the methyl formate and to promote extraction of the methanol to provide an overhead extract comprising isobutylene, methyl tertiary butyl ether and a minor amount of water, and a bottoms raffinate comprising methanol, water, alkali such as sodium formate and a minor amount of methyl tertiary butyl ether;

f) continuously charging said extract to a methyl tertiary butyl ether distillation zone and separating it therein into a lower boiling distillation fraction comprising isobutylene and water and a higher boiling distillation fraction consisting essentially of methyl tertiary butyl ether;

g) continuously charging the lower boiling distillation fraction to a decantation separation zone and separating it therein into an isobutylene fraction and a water fraction; and h) continuously recycling a portion of said isobutylene fraction to the methanol extraction zone.

DETAILED DESCRIPTION OF THE PRESENT INVENTION

Peroxide Decomposition

When the tertiary butyl alcohol feedstock to be used in the preparation of methyl tertiary butyl ether is tertiary butyl alcohol contaminated with peroxides such as tertiary butyl hydroperoxide, ditertiarybutyl peroxide, allyl tertiary butyl peroxide, etc., the feedstock is treated for the substantially complete removal of the peroxide contaminants before it is charged to the methyl tertiary butyl ether etherification zone, as shown, for example, in Kruse et al. U.S. Pat. No. 5,243,091.

The Etherification Reaction Catalyst

In accordance with the MTBE manufacture and purification method of the present invention, an etherification reaction zone containing a bed of etherification catalyst is utilized. A wide variety of etherification catalysts can be used for this purpose, such as supported phosphorus acid-type catalysts. A preferred catalyst is a sulfonic acid resin etherification catalyst such as a sulfonated polystyrene resin cross-linked with divinyl benzene.

Any suitable strongly acidic ion exchange resin etherification catalyst may be used for this purpose, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

Also, Kieselguhr impregnated with phosphoric acid as disclosed in Frolich U.S. Pat. No. 2,282,469, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc., may be used.

Zeolites as disclosed in Japanese Patent 0007432 or aluminosilicate zeolites as disclosed in Chang et al. U.S. Pat. No. 4,058,576 may also be used.

The reaction conditions to be utilized when reacting methanol with tertiary butyl alcohol in the presence of a sulfonic acid resin etherification catalyst of the type disclosed include a reaction temperature of about 90° to about 140° C., a pressure of about 30 to about 500 psia and a space velocity of about 0.5 to about 20 volumes of feed per volume of etherification catalyst per hour.

BRIEF DESCRIPTION OF THE DRAWING

The drawing is a schematic flow sheet with conventional parts omitted showing the general reaction and recovery sequence comprising the process of the present invention for the manufacture and purification of methyl tertiary butyl ether.

DESCRIPTION OF THE PREFERRED EMBODIMENT

Turning now to the drawing, there is shown a schematic flow sheet illustrating the preferred method for the practice of the process of the present invention. In the figure, conventional parts, such as valves, pumps, temperature control sensors, pressure sensors, heaters, coolers, flow control regulation apparatus, reflux condensers, reboilers, etc., have been omitted.

In accordance with the present invention, there is provided an etherification reaction zone 10 containing a bed of solid etherification catalyst. Any suitable etherification catalyst may be used such as, for example, a solid resin etherification catalyst of the type described above, such as a strongly acidic ion exchange resin consisting essentially of sulfonated polystyrene crosslinked with divinyl benzene (e.g., Dowex 50, Nalcite HCR, Amberlyst 15, etc.). As another example, the catalyst may be a fluorophosphoric acid-on-titania catalyst of the type disclosed in Knifton et al. U.S. Pat. No. 4,822,921 or a heteropoly acid such as 12-tungstophosphoric acid or 12-molybdophosphoric acid supported on an inert support such as titania.

Substantially peroxides-free tertiary butyl alcohol is continuously charged by a line 17 leading to a manifold 12, Methanol is continuously charged to the manifold 12 by a line 15. The flow of methanol and tertiary butyl alcohol to the manifold 12 through the lines 15 and 17 is regulated so that a molar excess of methanol is present in the line 14 leading to the etherification reaction zone 10, such as, for example, a molar ratio of about 1.1 to about 3 moles of methanol per mol of tertiary butyl alcohol.

Within the etherification reaction zone 10, the feed mixture is brought into contact with a bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C. and still more preferably from about 90° to about 130° C. When the catalyst is a supported phosphorus acid-type catalyst, the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 10 and, more preferably from about 1 to about 4 volumes of feed mixture per volume of etherification catalyst per hour.

Within the etherification reaction zone 10, methanol will react with the tertiary butyl alcohol to form methyl tertiary butyl ether which will be contained in a reaction product discharged from the etherification reaction zone 10 by way of a line 20 leading to a first methyl tertiary butyl ether (MTBE) distillation zone 30.

As a specific example, when the solid etherification catalyst is a sulfonic acid resin such as Amberlyst 15 and when the molar ratio of methanol to tertiary butyl alcohol in the feed mixture charged to the etherification reaction zone 10 by the line 14 is about 2.0 moles of methanol per mole of tertiary butyl alcohol, and the reaction is conducted at a temperature of about 110° C. at a feed rate of about 2.0 volumes of feed mixture per volume of catalyst per hour.

The etherification reaction product charged to the first MTBE distillation zone 30 by way of the charge line 20 is fractionated therein under distillation conditions including a liquid reflux temperature of about 30° to about 100° C., and more preferably about 40° to about 80° C., a reboiler temperature of about 80° to about 115° C., and more preferably from about 95° to about 105° C., and a pressure of about 15 to about 60 psia, the distillation condition being selected such that substantially all of the MTBE in the etherification reaction product 20 is taken overhead from the first distillation zone 30 by a line 32. As a consequence, the first lower boiling (lighter) distillation fraction 32 taken overhead from the distillation zone 30 will comprise substantially all of the isobutylene and substantially all of the methyl tertiary butyl ether and some of the methanol and acidic by-products charged to the first distillation zone 30. The higher boiling (heavier) distillation fraction 34 discharged from the first MTBE distillation zone 30 will comprise methanol, tertiary butyl alcohol and water.

In accordance with the present invention, the lower boiling (lighter) distillation fraction 32 together with recycle isobutylene charged by a recycle line 83 is charged through line 41 to a methanol solvent extraction zone 50 where it is counter-currently contacted with alkaline water introduced into the solvent extraction zone 50 by a charge line 52.

An aqueous solution of an alkali 54 such as sodium hydroxide, sodium carbonate, potassium hydroxide, etc., is charged to the solvent extraction tower 50 at a charge point adjacent the top thereof but at least about 1 to 3 stages below the charge point 52 for the alkaline wash water; the alkaline solution being charged in an Mount sufficient to substantially completely neutralize the acidic by-products, including methyl formate introduced into the solvent extraction tower 50 by the line 41. For example, an aqueous solution of sodium hydroxide containing from about 10 to 50 wt. % of sodium hydroxide may be charged by the line 54.

Within the methanol solvent extraction zone 50, solvent extraction conditions are established for countercurrent solvent extraction including a ratio of water to extraction feed mixture within the range of about 2 to 20 parts of extraction feed per volume of water, and more preferably about 5 to about 10 volumes of extraction feed per volume of water. Extraction conditions to be established may suitably include a temperature of about 20° to about 60° C., and more preferably from about 30° to about 40° C., and a pressure of about 50 to about 500 psia, and more preferably from about 50 to about 150 psia.

As a consequence, a supernatant extract substantially completely free from acidic by-products will be formed which is withdrawn from the methanol solvent extraction zone 50 by line 60 leading to second methyl tertiary butyl ether distillation zone 62. The raffinate is discharged from the solvent extraction zone 50 by way of a bottoms line 64 and will comprise methanol, water, alkali, including alkali formates and a minor amount of methyl tertiary butyl ether.

Within the second methyl tertiary butyl ether purification distillation zone 62, distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a lower boiling second distillation fraction 66 discharged from the second distillation zone 62. A higher boiling second distillation fraction 68 consisting essentially of product, namely methyl tertiary butyl ether is discharged from the second distillation zone 62 adjacent the bottoms thereof.

The second lower boiling distillation fraction 66 will comprise a mixture of isobutylene and water and suitably charged to a decantation zone 80 where it can settle to form a supernatant isobutylene phase withdrawn from the decantation zone 80 by way of a line 82. Water is discharged from the decantation zone 80 by way of a water discharge line 84 and is disposed of in any suitable manner. Preferably, all or a part of the water discharged by the line 84 is recycled to the solvent extraction zone 50 by the alkaline water charge line 52. A portion of the isobutylene in the line 82 is recycled by way of manifold 86, and line 83 to the solvent extraction zone 50. Suitably, about 10 to about 15 wt. % of the isobutylene in line 82 is discharged from manifold 86 as the first isobutylene recycle fraction 83 and about 90 to about 85 wt. % is discharged as a second isobutylene recycle fraction 42.

In accordance with the present invention, the second isobutylene recycle fraction 42 is charged to a manifold 45. Methanol is added to manifold 45 by line 44 and mixed with the second isobutylene recycle fraction 42. The resultant reaction mixture is charged through line 46 to manifold 48 and then through line 90 to an isobutylene reactor 40 containing a bed of solid resin etherification catalyst such as a bed of Amberlyst 15 sulfonated polystyrene-divinyl benzene copolymer acidic ion exchange resin. Within the isobutylene conversion reactor 40 etherification reaction conditions are established including, for example, a temperature of about 35° to about 130° C., and more preferably from about 40° to about 70° C., a pressure of about 50 to about 500 psia, and more preferably from about 150 to about 250 psia, and a contact time of about 0.5 to about 4 volumes of reaction mixture per volume of solid resin etherification catalyst per hour. As a consequence, a portion of the methanol and isobutylene contained in the first distillation fraction 32 will be converted to methyl tertiary butyl ether. Typically, the conversion will amount to about 30 to about 60 wt. %, based on the isobutylene.

As a consequence, an isobutylene conversion product will be formed in the isobutylene reactor 40 and is discharged by a line 42. The isobutylene conversion product will normally contain from about 0 to about 10 wt. % of isobutylene, about 75 to about 85 wt. % of methyl tertiary butyl ether and from about 10 to about 15 wt. % of methanol. The composition of a typical isobutylene conversion product may be characterized as follows:

| ISOBUTYLENE CONVERSION PRODUCT | |
|---|---|
| Component | wt. % (Approx.) |
| Isobutylene | 5.4 |
| MTBE | 79.5 |
| Methanol | 12.2 |
| Other[1] | 2.9 |

[1]Includes acidic by-products

The isobutylene conversion product is discharged from the isobutylene reactor 40 by a line 42 leading to heat exchanger 94 where the isobutylene conversion product is cooled to a temperature of about 30° to about 100° C. The cooled isobutylene conversion product is discharged from the heat exchanger 94 by a line 96 leading to a manifold 97. About 10 to 20 mol % of the isobutylene conversion product is discharged from the manifold 97 by a line 98 and is suitably recycled to the methanol extractor 50. The remainder of the isobutylene conversion product is discharged from the manifold 97 by a line 95 leading to the manifold 48 where the remainder of the isobutylene conversion product as added to the isobutylene reaction mixture 90 as a diluent to moderate the reaction.

OPERATION

In accordance with a preferred embodiment of the present invention, substantially peroxides-free tertiary butyl alcohol product 17 is charged to the manifold 12 together with a methanol feedstock 15 in amounts such that the charge ratio of methanol to tertiary butyl alcohol in the feed line 14 amounts to about 2 moles of methanol per mole of tertiary butyl alcohol.

The feed mixture is discharged from the manifold 12 by a line 14 leading to etherification reaction zone 10 containing a bed of a suitable etherification catalyst, such as Amberlyst 15 catalyst. Within the etherification reaction zone 10, the feedstock is passed through the etherification reaction bed on a continuous basis under reaction conditions, as described above, to thereby provide a reaction product having the following composition:

| ETHERIFICATION REACTION ZONE 10 REACTION PRODUCT | |
|---|---|
| Component | wt. % (Approx.) |
| Water | 14.0 |
| Methanol | 27.6 |
| Isobutylene | 3.0 |
| TBA[1] | 14.1 |
| MTBE[2] | 34.5 |
| Other[3] | 6.8 |

[1]Tertiary butyl alcohol
[2]Methyl tertiary butyl ether
[3]Includes the methyl formate, acetone, propanol, ditertiary butyl peroxide, tertiary butyl formate, etc., initially present in the tertiary butyl alcohol feedstock.

The etherification zone reaction product is discharged from the reaction zone 10 by a line 20 leading to first methyl tertiary butyl ether distillation zone 30 where the reaction product 20 is separated into a first lower boiling distillation fraction 32 comprising about 6.5 wt. % isobutylene, about 16.5 wt. % methanol, about 75 wt. % MTBE and about 2 wt. % other components, including acidic by-products, and a first higher boiling fraction comprising about 37 wt. % methanol, about 26.0 wt. % tertiary butyl alcohol, about 25.5 wt. % water, 11 wt. % isopropanol and about 0.5 wt. % of other components.

The first lower boiling distillation fraction 32 along with recycle isobutylene 83 is continuously charged to a manifold 36. The mixture is discharged from the manifold 36 by a feed line 41 leading to methanol extraction zone 50 in the ratio of about 2 parts of first lower boiling distillation fraction 32 per part of recycle isobutylene. An alkaline water stream is charged to the methanol extraction zone 50 by a water charge line 52 and a stream of an aqueous solution of an alkali such as sodium hydroxide is charged by a line 54 at a charge point at least 1 to 3 stages below the charge point for the alkaline wash water 52; the streams 52 and 54 being charged in an amount such that the ratio of water to isobutylene in the methanol extraction zone 50 is in the range of about 0.05 to about 0.3 parts of water per part of extraction zone feed mixture.

Within the methanol extraction zone 50, the methanol is extracted from the isobutylene conversion product under extraction conditions as described above to thereby provide an overhead extract fraction 60 substantially free from acidic by-products comprising isobutylene and methyl tertiary butyl ether and residual quantities of water and a raffinate 64 comprising methanol, water and residual quantities of isobutylene, alkali and methyl tertiary butyl ether.

The extract is fed by a line 60 to a second methyl tertiary butyl ether purification distillation zone 62 where it is resolved by distillation into a second lower boiling distillation fraction 66 comprising isobutylene and water and into a second higher boiling distillation fraction 68 consisting essentially of methyl tertiary butyl ether which is discharged as product.

The second lower boiling distillation fraction 66 is charged to a decantation separation zone 80 where it is permitted to settle and is resolved into an isobutylene fraction 82 and a first water fraction 84 which is disposed of in any suitable manner. Preferably, all or a part of the water discharged by the line 84 is recycled to the solvent extraction zone 50 by the alkaline water charge line 52. A portion of the isobutylene in the line 82 is recycled by way of manifold 86, and line 83 to the solvent extraction zone 50. Suitably, about 10 to about 15 wt. % of the isobutylene in line 82 is discharged from manifold 86 as the first isobutylene recycle fraction 83 and about 90 to about 85 wt. % is discharged as a second isobutylene recycle fraction 42.

The isobutylene fraction 82 is suitably charged to the isobutylene conversion zone 40 in admixture with methanol charged to manifold 45 through line 44.

The raffinate 64 is continuously discharged by a line 64.

Within isobutylene conversion zone 40, the feed mixture 90 is brought into contact with a solid resin etherification catalyst, such as Amberlyst 15 catalyst, under conversion conditions, as described above, to thereby convert about 50 wt. % of the isobutylene and a portion of the methanol in the first distillation fraction to MTBE and to form an isobutylene conversion product which is discharged from the isobutylene reaction zone 40 by a line 92 and which typically has the following composition:

| ISOBUTYLENE CONVERSION FEED AND PRODUCT, wt. % | | |
|---|---|---|
| Component | Approx. wt. % Feed | Approx. wt. % Product |
| Isobutylene | 11 | 5.5 |
| MTBE | 71 | 79.5 |
| Methanol | 15 | 12 |
| Other[1] | 3 | 3 |

[1]Includes acidic components

The isobutylene conversion product is discharged from the isobutylene reactor 40 by a line 42 leading to heat exchanger 94 where the isobutylene conversion product is cooled to a temperature of about 30° to about 100° C. The cooled isobutylene conversion product is discharged from the heat exchanger 94 by a line 96 leading to a manifold 97. About 10 to 20 mol % of the isobutylene conversion product is discharged from the manifold 97 by a line 98 and is suitably recycled to the methanol extractor 50. The remainder of the isobutylene conversion product is discharged from the manifold 97 by a line 95 leading to the manifold 48 where the remainder of the isobutylene conversion product as added to the isobutylene reaction mixture 90 as a diluent to moderate the reaction.

Having thus described our invention, what is claimed is:

1. In a method for continuously preparing methyl tertiary butyl ether from methanol, tertiary butyl alcohol and isobutylene, wherein an etherification reaction product is obtained comprising isobutylene, methanol, acidic by-products comprising methyl formate and methyl tertiary butyl ether, the improvement which comprises:

a) charging said etherification reaction product to a first MTBE distillation zone and fractionating it therein to provide a first lower boiling distillation fraction comprising isobutylene, methyl tertiary butyl ether, methanol and acidic by-products and also to provide a higher boiling distillation fraction comprising methanol, tertiary butyl alcohol and water;

b) continuously charging said first lower boiling distillation fraction to a methanol extraction tower adjacent the bottom thereof;

c) continuously charging wash water to said methanol extraction tower adjacent the top thereof;

d) continuously charging an aqueous solution of an alkali to said methanol extraction tower adjacent the top thereof but below the charge point for the wash water, in an amount sufficient to substantially completely neutralize the said acidic by-products, to thereby counter-currently contact the etherification reaction product to provide an overhead extract substantially free from acidic by-products comprising isobutylene, methyl tertiary butyl ether and a minor amount of water, and a bottoms raffinate comprising methanol, water, alkaline by-products and a minor amount of methyl tertiary butyl ether; and e) continuously separating said extract into a fraction comprising isobutylene and water and a fraction consisting essentially of methyl tertiary butyl ether.

2. A method as in claim 1 wherein the methanol extraction tower contains from about 4 to about 10 theoretical trays and wherein the alkali solution is charged to the methanol extraction tower about 1 to about 3 theoretical trays below the charge point for the wash water.

3. A method as in claim 2 wherein alkali is sodium hydroxide.

4. A method as in claim 3 wherein sodium hydroxide is introduced as a solution of about 10 to about 50 wt. % of sodium hydroxide in water.

5. In a method for continuously preparing methyl tertiary butyl ether from methanol, tertiary butyl alcohol and isobutylene, wherein an etherification reaction product is obtained comprising isobutylene, methanol, acidic by-products comprising methyl formate and methyl tertiary butyl ether, the improvement which comprises:

a) charging said etherification reaction product to a first MTBE distillation zone and fractionating it therein to provide a first lower boiling distillation fraction comprising isobutylene, methyl tertiary butyl ether, methanol and acidic by-products and also to provide a higher boiling distillation fraction comprising methanol, tertiary butyl alcohol and water;

b) continuously charging said first lower boiling distillation fraction to a methanol extraction tower adjacent the bottom thereof;

c) continuously charging alkaline wash water to said methanol extraction tower adjacent the top thereof in the ratio of about 2 to about 20 volumes of first lower boiling distillation fraction per volume of water under extraction conditions including a temperature of about 20° to about 60° C. and a pressure of about 50 to 500 psia;

d) continuously charging an aqueous solution of an alkali to said methanol extraction tower adjacent the top thereof but below the charge point for the wash water, in an amount sufficient to substantially completely neutralize the said acidic by-products, to thereby counter-currently contact the etherification reaction product to provide an overhead extract substantially free from acidic by-products comprising isobutylene, methyl tertiary butyl ether and a minor amount of water, and a bottoms raffinate comprising methanol, water, alkaline by-products and a minor amount of methyl tertiary butyl ether; and e) continuously separating said extract into a fraction comprising isobutylene and water and a fraction consisting essentially of methyl tertiary butyl ether.

6. A method as in claim 5 wherein the methanol extraction tower contains from about 4 to about 10 theoretical trays and wherein the alkali solution is charged to the methanol extraction tower about 1 to about 3 theoretical trays below the charge point for the wash water.

7. A method as in claim 2 wherein alkali is sodium hydroxide, wherein the methanol extraction tower contains from about 3 to about 10 theoretical trays and wherein the sodium hydroxide solution is charged to the methanol extraction tower about 1 to about 3 theoretical trays below the charge point for the wash water.

8. A method as in claim 3 wherein sodium hydroxide is introduced as a solution of about 10 to about 50 wt. % of sodium hydroxide in water.

9. A method as in claim 8 wherein the extraction conditions include a temperature of about 30° to about 40° C. and a pressure of about 50 to 150 psia.

* * * * *